(12) United States Patent
Kondejewski et al.

(10) Patent No.: US 6,872,806 B1
(45) Date of Patent: Mar. 29, 2005

(54) POLYPEPTIDE COMPOSITIONS FORMED USING A COILED-COIL TEMPLATE AND METHODS OF USE

(75) Inventors: Leslie H. Kondejewski, St. Lazare (CA); Randall T. Irvin, Sherwood Park (CA); Robert S. Hodges, Edmonton (CA)

(73) Assignee: The Governors of the University of Alberta, Edmonton ( * ) Notice: Subject to any disclaimer, the term of this patent is extended or adjusted under 35 U.S.C. 154(b) by 0 days.

(21) Appl. No.: 09/603,832

(22) Filed: Jun. 26, 2000

Related U.S. Application Data (60) Provisional application No. 60/141,203, filed on Jun. 25, 1999.

(51) Int. Cl.[7] .................. A61K 38/00; A61K 39/00; C12P 21/08
(52) U.S. Cl. .............. 530/333; 300/324; 300/387.3; 300/388.2; 424/184.1; 424/185.1; 435/7.1; 435/69.7
(58) Field of Search .............. 435/7.1, 69.7, 435/320.1, 325, 252.3, 254.11, 69.1; 424/184.1, 185; 530/300, 324, 333, 387.3, 388.2, 350; 536/25.3, 23.5

(56) References Cited

U.S. PATENT DOCUMENTS

| | | | |
|---|---|---|---|
| 5,773,572 A | * | 6/1998 | Fishleigh et al. ........... 530/324 |
| 5,792,901 A | * | 8/1998 | Prusiner et al. ............... 800/2 |
| 5,824,483 A | | 10/1998 | Houston, Jr. et al. ........ 435/7.1 |
| 5,837,816 A | | 11/1998 | Ciardelli et al. ............. 530/350 |
| 5,856,928 A | * | 1/1999 | Yan ............................. 364/496 |
| 5,962,669 A | * | 10/1999 | Prusiner et al. ............. 536/23.5 |
| 6,174,528 B1 | | 1/2001 | Cooper et al. |
| 6,242,213 B1 | * | 6/2001 | Anderson ................... 435/69.1 |

FOREIGN PATENT DOCUMENTS

| WO | WO 93/15110 | 8/1993 |
|---|---|---|
| WO | WO 95/31480 | 11/1995 |

OTHER PUBLICATIONS

Prusiner et al. Jun. 3, 1997, Database: Issued_Patents_AA, Accession No.: US–08–868–162A–21, Seq ID No.: 5 alignment result 6.*

Prusiner et al. Jun. 3, 1997, Database: Issued_Patents_AA, Accession No.: US–08–868–162A–21, Seq ID No.: 7 alignment result 6.*

Fishleigh et al. Jun. 2, 1994, Database: Issued_Patents_AA, Accession No.: US–08–244–701B–36, Seq ID No.: 6 alignment result 1.*

* cited by examiner

*Primary Examiner*—Jon Weber
*Assistant Examiner*—Rita Mitra
(74) *Attorney, Agent, or Firm*—Fish & Richardson P.C.

(57) ABSTRACT

The invention relates to the use of constrained coiled-coil polypeptides to mimic α-helical structural elements of native proteins. These constrained peptidyl mimetics are used to generate and/or identify ligands, which selectively bind the α-helical segment contained in the native protein.

30 Claims, 3 Drawing Sheets

$(ab_1c_1de_1f_1g_1)_1 \ (ab_2c_2de_2f_2g_2)_2 \ \ldots \ (ab_ic_ide_if_ig_i)_n$

Fig. 3

```
                     143                  156
PrPc H1  Sequence:   N D W E D R Y Y R E N M Y R
                     d e f g a b c d e f g a b c
H1  Construct:  H2N-A L D W E I R Y L E N I Y R
```

Fig. 4A

```
                                200                  219
PrPc H3  Sequence:               E T D V K M M E R V V E Q M C V T Q Y Q
                         a b c d e f g a b c d e f g a b c d e f g a b c d e f g a
H3  Construct:   H2N-    [C A A L] E T D [I] K M [L] E R V [I] E Q [L] C V T [I] Y Q [L A A A I R R R R] -amide
Heterodimer  BBA-NleG-   [C A A L] E T D [I] K M [L] E R V [I] E Q [L] C V T [I] Y Q [L A A A I R R R R] -NH2
                          |
             Ac-         [C A A L] E T D [I] K M [L] E R V [I] E Q [L] C V T [I] Y Q [L A A A I R R R R] -NH2
```

Fig. 5

POLYPEPTIDE COMPOSITIONS FORMED USING A COILED-COIL TEMPLATE AND METHODS OF USE

This application claims the benefit of U.S. Provisional Application No. 60/141,203 filed Jun. 25, 1999, incorporated herein by reference in its entirety.

FIELD OF THE INVENTION

The present invention relates to synthetic polypeptide compositions comprised of a selected epitope from an α-helical surface region of a protein inserted into a coiled-coil polypeptide template. The epitope constrained in the template is displayed for presentation as an antigen. In this way, conformation-specific antibodies can be generated for use as therapeutic and diagnostic ligands.

BACKGROUND OF THE INVENTION

Protein binding or protein—protein interactions can be broadly defined as the discrete interaction of the surface of one protein with the surface of another protein. Such discrete interaction arises when residues of one protein are proximally located to residues of another protein and attractive forces between the residues such as van der Waals forces, ionic bonds ard hydrogen bonds exist. Specific protein—protein interactions which occur in higher living organisms include, for example, a receptor-binding protein binding to a receptor; a pathogen antigen binding to a host cell receptor and protein interactions at cellular attachment sites.

Proteins and in particular pathogenic proteins such as bacteria, fungi, parasites, and viruses express specific antigens on their surface for interaction. Typically, there are specific sites on antigens, hereinafter referred to as binding epitopes or epitopes, which bind to a complementary portion of a cellular protein called a receptor site.

Identification and/or preparation of compounds, e.g., peptide or polypeptide compounds, that specifically either simulate, that is mimic, or block protein—protein interactions in cells is desirable for a variety of therapeutic and diagnostic purposes and considerable effort has been made to identify protein epitopes. The epitope, in order to be useful in therapeutic and diagnostic fields, needs to be displayed and presented for interaction with other proteins.

SUMMARY OF THE INVENTION

Accordingly, it is an object of the invention to provide a synthetic polypeptide composition for display and presentation of an epitope from a selected protein.

It is another object of the invention to provide a synthetic polypeptide composition effective to generate antibodies to a specific conformation of a protein epitope.

It is a further object of the invention to provide a synthetic polypeptide that displays an epitope for generation of antibodies that recognize and bind to the native protein from which the epitope is selected.

It is a further object of the invention to provide a method to stabilize an epitope from an α-helical protein that in its native state is not in a coiled-coil conformation.

Accordingly, in one aspect, the invention includes a coiled-coil polypeptide composition, comprised of a template of the form $(ab_ic_ide_if_ig_i)_n$, where n is at least three, a and d are amino acids selected from the group consisting of leucine, isoleucine, valine, phenylalanine, methionine, tyrosine, and derivatives thereof. The sequence formed by the positions $(b_ic_ie_if_ig_i)$, is a sequence of amino acids from a solvent-accessible region of an epitope from a selected protein, which in one embodiment, is normally not in a coiled-coil conformation.

In one embodiment, a is isoleucine and d is leucine.

In another embodiment, the coiled-coil polypeptide is comprised of two polypeptide chains arranged in a parallel configuration.

In still another embodiment, n is between about 3 and about 20, and more preferably between about 5 and about 10.

The epitopes, in yet another embodiment, are selected from α-helical surface regions of cellular prion protein, or, alternatively, from exposed surface regions of infectious prion protein. The selected epitopes can be, for example, the epitopes represented by SEQ ID NO:5, SEQ ID NO:6, or SEQ ID NO:7. The cellular prion protein can be from any species, and in preferred embodiments is selected mouse, hamster, bovine, ovine and human cellular prion protein.

In another aspect, the invention includes a method for stabilizing and displaying an epitope in a synthetic α-helical, coiled-coil polypeptide. The method includes preparing a coiled-coil polypeptide comprised of a template of the form described above.

In yet another aspect of the invention, a method for preparing antibodies specific to a particular conformation of a protein epitope is described. The method includes preparing a coiled-coil polypeptide comprised of a template described above.

These and other objects and features of the invention will be more fully appreciated when the following detailed description of the invention is read in conjunction with the accompanying drawings.

BRIEF DESCRIPTION OF THE SEQUENCES

SEQ ID NO:1 is the sequence of the 124–226 fragment of human prior protein;

SEQ ID NO:2 is the sequence of the 124–226 fragment of mouse prion protein;

SEQ ID NO:3 is the sequence of the 124–226 fragment of ovine prion protein;

SEQ ID NO:4 is the sequence of the 124–226 fragment of bovine prion protein;

SEQ ID NO:5 is the α-helical-1 region of mouse prion protein;

SEQ ID NO:6 is the α-helical-2 region of mouse prion protein;

SEQ ID NO:7 is the α-helical-3 region of mouse prion protein;

SEQ ID NO:8 is the sequence formed by inserting the α-helical-1 region of mouse prion protein into the α-helical template; and SEQ ID NO:9 is the sequence formed by inserting the α-helical-3 region of mouse prion protein into the α-helical template.

DETAILED DESCRIPTION OF THE INVENTION

I. Definitions

The terms "peptide" and "polypeptide", used interchangeably, designate a chain of amino acid based polyamides. The chain can vary in length anywhere from 2 amino acids to 100 or more amino acids. Further, the term "heterodimer polypeptide" refers to two associated non-identical polypeptide chains. The term "homodimer polypeptide" refers to two associated identical polypeptide chains.

"Eptiope" as used herein describes the amino acid component of a molecule and the structural component of a molecule that is responsible for specific interactions with corresponding antibody (immunoglobulin) molecules elicited by the same or related antigen. Epitopes can be either linear or conformational. Linear epitopes refer to contiguous amino acid residues in a sequence whereas conformational epitopes are formed from non-contiguous amino acids in the sequence and are dependent on both the secondary and tertiary structure of the molecule.

"Corresponds to" and "derived from" refer to an amino acid sequence based on a first amino acid sequence, where some residues in the first amino acid sequence are replaced or substituted with other amino acids residues, and where such substitutions do not alter the biological function of the amino acid sequence.

A "derivative", as in a derivative of an amino acid, refers to an amino acid that has been modified in such a way to alter or change the chemical structure, where such an alteration does not appreciably effect the function or activity of a polypeptide that includes the altered amino acid in place of the native amino acid.

The terms "solvent-exposed" and "solvent-accessible" are used interchangeably, and refer to the amino acid residues in an α-helical coil or coiled-coil polypeptide that are displayed on the outward facing aspects of the coil and available for interaction with a protein.

Unless otherwise indicated, the sequence for peptides and polypeptides is given in the order from the amino terminus to the carboxyl terminus. All amino acid residues identified herein are in the natural or L-configuration unless otherwise specified. In keeping with standard peptide nomenclature, abbreviations for amino acid residues are standard 3-letter and/or 1 letter codes commonly used in the art.

II. General Coiled-Coil Compositions

The present invention relates to polypeptide compositions where the solvent-accessible residues of an epitope from an α-helical region of a protein that is normally not in a coiled-coil conformation is inserted into a conformationally-restricted, stabilized coiled-coil template. As will be described below, the template, or scaffold, allows for presentation of the solvent-accessible amino acid residues of the epitope in a fixed coiled-coil conformation. The coiled-coil has a sequence that contains "invariant" positions and "variable" positions. The invariant positions maintain or stabilize the peptide in an α-helical coiled-coil conformation. In the variable positions, any desired epitope sequence (s) is inserted, as will be described. Also as will be described below, α-helical polypeptides formed based on the template can be used to form, a two-stranded coiled-coil, where the strands are either homodimeric or heterodimeric and can be in a parallel or anti-parallel orientation. A single-polypeptide α-helical chain can also be constructed using the template, where the single polypeptide chain may fold back on itself in an anti-parallel fashion to form the coiled-coil.

Peptides in an α-helical coiled-coil conformation reversibly bind to each other in a characteristic manner and to one another in a characteristic manner that is determined by the identity of the residues at the invariant positions of the peptide. The tertiary structure of a coiled-coil α-helix is such that seven amino acid residues in the primary sequence correspond to approximately two turns of the coiled-coil. A primary amino acid sequence giving rise to an α-helical coiled-coil conformation may be broken down into units of seven residues, termed heptads.

Figure 1:
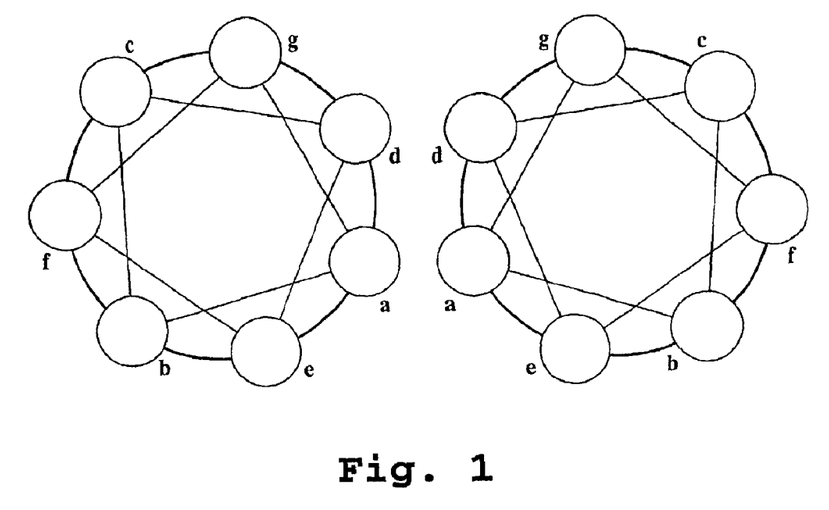
FIG. 1 is a helical wheel representation of a heptad unit in an α-helical coiled-coil.

FIG. 1 shows a helical wheel representation of an α-helix in a coiled-coil. The positions of the side chains forming the heptad unit are identified by the letters a, b, C, d, e, f, and g. In an ideal α-helix, there are 3.6 residues per complete turn, or a rotation of 100° per residue. As can be envisioned from the drawing, the a and d side chains, or residues, lie along one side of the helix, which is referred to herein as the internal, or hydrophobic core region. The amino acid residues at positions b, c, e, f, and g are said to lie on the external, exposed, or "solvent-accessible", region of the helix.

Figure 2:
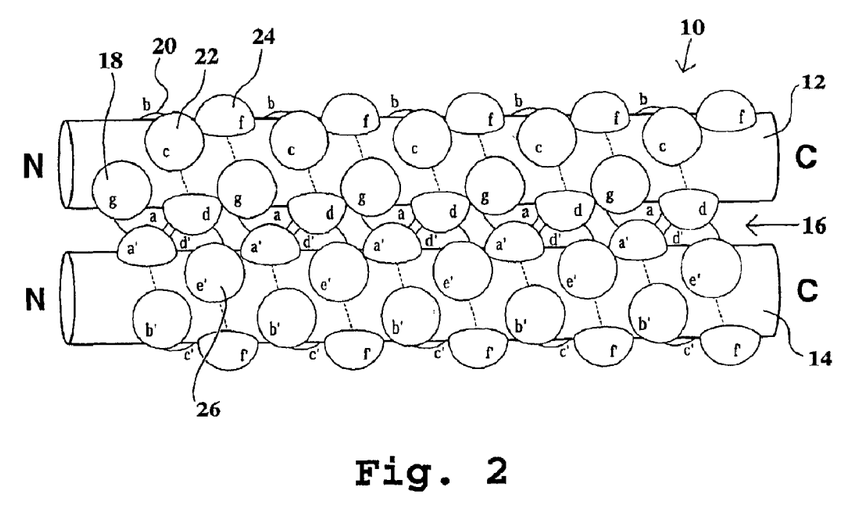
FIG. 2 is a schematic representation of a coiled-coil dimerization motif used as the α-helical template to stabilize linear native α-helical peptide sequences in an α-helical conformation.

These regions are illustrated more clearly in FIG. 2, where two α-helical polypeptide chains 12, 14 are shown in contact in a parallel configuration. In a parallel configuration, two polypeptide helices are aligned such that they have the same orientation, amino-terminal (N) to carboxy-terminal (C). In an anti-parallel configuration, the helixes are arranged such that the amino-terminal end one helix is aligned with the carboxy-terminal end of the other helix. In FIG. 2, the two helices 12, 14 are in contact along the face defined by the a and d (or a' and d' on the second helix) positions, e.g., region 16, referred to herein as the "internal" region of a coiled-coil. Residues in the a and d positions are preferably regularly repeating amino acid residues that are hydrophobic to drive the dimerization and stabilize the structure. These hydrophobic residues are "invariant" in the template in that they are selected from the amino acids leucine, isoleucine, valine, phenylalanine, methionine, tyrosine, or derivatives thereof. In a preferred embodiment, position a is isoleucine and position d is leucine.

With continuing reference to FIG. 2, residues at positions b, c, e, f, and g, some of which are identified in FIG. 2 by 18, 20, 22, 24, 26, lie at the outward-facing aspects of the coiled-coil scaffold, and are in contact with the solvent in which the coiled-coil scaffold is suspended. These positions are referred to herein as "solvent-accessible" residues.

Figure 3:
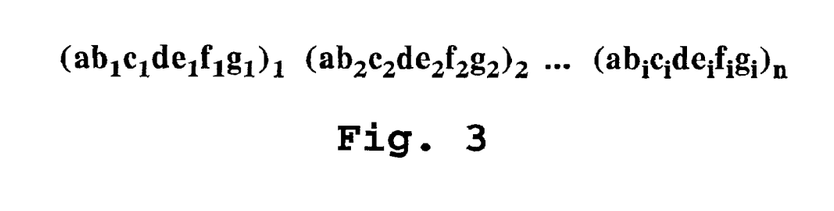
FIG. 3 is a linear representation of a single chain of the α-helical coiled-coil template.

The template for use in she invention is depicted in FIG. 3 in a linear arrangement rather than a coiled-coil for viewing simplicity. Each polypeptide chain in the coiled-coil is of the form $(ab_ic_ide_if_ig_i)_n$. The variable n can be from about 3 to about 50, more preferably from about 3 to about 20, and even more preferably, n is from about 5 to about 10. In FIG. 3, the heptads for n=1 and n=2 are shown. Positions a and d in each heptad of the polypeptide are amino acids selected from the group recited above, and are preferably isoleucine and leucine, respect vely. Positions $(b_ic_ie_if_ig_i)_n$ correspond to the "solvent-accessible" positions of an epitope sequence from a selected protein, as will now be described.

Epitopes, that is the structural component of a molecule, such as a polypeptide or protein, that is responsible for specific interactions with corresponding antibody molecules, are known and have been elucidated for a wide variety of proteins. For example, epitopes of proteins from pathogenic microorganisms have been identified for feline leukemia virus (Elder, J. H. et al., *J. Virol.* 61: 8–15, 1987), hepatitis B (Gerin, J. L., et s0 al., *Proc. Natl. Acad. Sci. USA* 80: 2365–2369 1983), *Plasmodium falciparum* (Cheung, A., et al., *Proc. Natl. Acad. Sci. USA* 83: 8328–8332, 1986), cholera toxin (Jacob, C. O., et al., *Eur. J. Immunol.* 16: 1057–1062, 1986) and others. The epitopes elicit a specific response and those which elicit a desired response can be identified by methodologies known to those of skill in the art. For example, U.S. Pat. No. 5,637,677 describes a method of identifying specific linear and constrained discrete portions of biologically active proteins involved in protein—protein interactions. In the present invention, the amino acids in the solvent-accessible positions b, c, e, f, and g of a selected epitope are inserted into the coiled-coil template in a corresponding position, $b_i$, $c_i$, $e_i$, $f_i$, $g_i$. The a and d positions from the epitope are replaced in favor of selected hydrophobic residues, for example, isoleucine and leucine, in the template. Thus, the selected epitope is inserted into the template discontinuously, as only the solvent-accessible, exposed residues of the epitope are inserted into the template.

The sequence of solvent-accessible residues of the epitope once inserted into the α-helical template is stabilized in an α-helical conformation for presentation of the epitope for subsequent interaction and binding. As such, the synthetic polypeptide is biologically active and mimics the biological activity and/or structure of the native α-helical protein. As will be described more fully below, using the template and a desired epitope, biologically active peptides can be constructed which act as ligands that act on mammalian cells by binding to the receptor sites of those cells to alter or affect their function or behavior, or to prevent the binding of the natural biologically active protein to the cellular receptor, thereby preventing the biologically active protein from affecting the cell. Additionally, synthetic polypeptides formed using the template and a desired epitope can be used to generate antibodies which are specific to and reactive with a conformational epitope present on the native protein from which the epitope is derived.

As will be seen in the examples set forth below, in one embodiment, a single epitope is inserted into the template. The single epitope can be inserted into the template one or more times, depending on the length of the epitope and on the desired function. For example, an epitope having a sequence of 42 amino acid residues, which corresponds to 6 heptad units, consists of 12 residues at positions a and d, and 30 residues at positions b, c, e, f, and g. The 30 residues at the solvent accessible positions b, c, e, f, and g are inserted into the template in-phase, that is, in a corresponding b, c, e, f, or g position. The a and d residues of the epitope are not necessarily incorporated into the template, since the template a and d positions are fixed, hydrophobic residues, such as isoleucine and leucine. Multiple polypeptides having the same epitope can be constructed, and two chains can interact, or be further assisted in their interaction by, for example a disulfide bridge, to form a stabilized, homodimeric coiled-coil polypeptide.

Studies were performed in support of the invention where coiled-coil synthetic polypeptides were constructed using epitopes from mouse prion proteins. More specifically, the solvent-accessible residues of epitopes derived from cellular prion protein, $PrP^c$, were inserted into the template. The synthetic polypeptides so formed act as peptidyl mimetics and are for use in identifying ligands that selectively recognize structural epitopes on $PrP^c$ under native conditions.

Prions (short for proteinaceous infectious particles) have been implicated in a number of inherited and infectious neurodegenerative disorders in livestock as well as in humans (see Pruisner et al. 1998 and references therein). Human diseases such as Creutzfeldt-Jacob disease (CJD), Gerstmann-Staussler-Scheinker in disease and fatal familial insomnia are believed to be prion diseases. Bovine spongiform encephalitis (BSE) and scrapie of sheep are examples of animal prion diseases, which are feared to be able to be transmitted to humans through ingestion of meat products. The prion diseases are all fatal and share similar pathological changes, where the presence of plaques and lesions in the brains of infected individuals are found. In afflicted humans or animals, the loss of physical coordination followed by dementia and death are characteristic of progression of the prion diseases.

It is widely accepted that prion proteins themselves, and not virus particles, are responsible for the prion diseases. It is believed that the normal prion protein, $PrP^c$, is transformed into an infectious form, $PrP^{sc}$, by means of a conformational change in the protein. Such conformational changes of prions have been demonstrated in vitro using cell-free systems with substantially purified components (Kocisko, D. A., et al., *Nature* 370:471–474, 1994) and in vivo using animal models (Telling, G. C., et al., *Science* 274:2079–2082, 1936). The conformational switch appears to be from the normal α-helical form of the protein ($PrP^c$) to an infectious β-sheet form of the protein ($PrP^{sc}$). Fourier-transform infrared (FTIR) and circular dichroism (CD) studies showed that $PrP^c$ contains about 40% α-helix and 3% β-sheet, whereas $PrP^{sc}$ is composed of about 30% α-helix and 45% β-sheet (Pan, K. M., et al., *Proc. Natl. Acad. Sci. USA* 90:10962–6, 1993, Pergami, P., et al. *Anal. Biochem.* 236:63–73, 1996). The two forms have distinct physical characteristics, with $PrP^c$ being soluble and sensitive to proteolytic digestion and $PrP^{sc}$ being water insoluble and resistant to proteolytic digestion. The insolubility of the $PrP^{sc}$ form is likely responsible for the characteristic formation of plaques in the brains of infected individuals. Further evidence for the role of a conformational switch from α-helix to β-sheet in prion diseases comes from work with peptides derived from the prion protein (Zhang, H., et al., *J. Mol. Biol.* 250:514–526, 1995). These peptides can exist in either an α-helical or β-sheet conformation depending on solvent conditions such as salt and organic solvent concentration as well as pH. Furthermore, these peptides can also form plaques or fibrils in vitro. It was recently shown that normal $PrP^c$ can be converted into two different forms of $PrP^{sc}$ depending on the type of abnormal prion used to initiate the conversion (Telling, G. C., et al., *Science* 274:2079–2082, 1996).

Prion protein is composed of approximately 250 residues, which is proteolytically processed to remove the 22-residue N-terminal signal peptide and 23 C-terminal amino acids after addition of the glycosylphosphatidylinositol anchor to Ser-231 (Prusiner, S. B., *Trends Biochem. Sci.* 21:482–487, 1996; Prusiner, S. B., *Science* 278:245–251, 1997). The processed protein contains a disulfide bond (179 to 214) and glycosylation sites at Asn-181 and Asn-197. The protease resistant core of prion protein is composed of residues 90–231, which is sufficient to transmit infectivity. The sequence of a prion protein for a number of animal species has been elucidated (Billeter, M. et al., *Proc. Natl. Acad. Sci.*

USA, 94:7281–7285, 1997), and partial fragments for some of the species are provided here as SEQ ID NOS:1–4. It has been shown that a truncated segment of a recombinant mouse prion protein, PrP (121–231), is an autonomous folding unit (Hornemann, S. et al., *J. Mol. Biol.* 262:214–619, 1996). Presumably the structure of this segment is similar to that found in PrP$^c$. This finding has led to the hypothesis that the conformational change leading to the infectious form PrP$^{sc}$ occurs in that segment. The NMR structure of the same segment of the mouse prion protein has been solved (Riek, R., et al., *Nature* 382:180–182, 1996). The three dimensional structure reveals the existence of three α-helices and an antiparallel two-stranded β-sheet (128–131 and 161–164). Helix-1 (residues 144–154; SEQ ID NO:5) is somewhat isolated, Helix-2 (residues 179–193; SEQ ID NO:6) and Helix-3 (residues 200–217; SEQ ID NO:7) interact more closely together and run anti-parallel. Helix-2 and Helix-3 are linked together by a disulfide bond. The two-stranded 3-sheet lies on Helix-2.

An essentially identical NMR structure has been determined for Syrian hamster prion protein (90–231) James, T. L., et al., *Proc., Natl. Acad. Sci.* 94:10086–91, 1997). The NMR solution structures of recombinant full-length prion protein from mouse (Riek, R., et al., *FEBS Lett.* 413:282–288, 1997) and Syrian hamster (Donne, et al., *Proc. Natl. Acad. Sci. USA* 94:13452–7, 1997) have subsequently been determined and show that the N termini of both these proteins have no defined elements of secondary structure and are highly flexible under the experimental conditions employed. Although these structures are similar, they differ in detail, which is interesting and most likely demonstrates the subtle dependency that the prion sequence has on the exact aqueous environment in which the structures were recorded. These findings support the contention that the major structural changes occurring in the conversion of PRP$^C$ to PrP$^{sc}$ occur within the residue 121–231 region.

In studies performed in support of the invention, peptidyl mimetics of the three α-helices, helix-1 (SEQ ID NO:5), helix-2 (SEQ ID NO:6) and helix-3 (SEQ ID NO:7) were designed. α-helices in proteins are typically 10 to 12 amino acid residues in length. These same segments as isolated peptides are generally devoid of structure and assume multiple random-like conformations under aqueous conditions. The segments can be constrained and stabilized using the template described herein, as will now be further described.

Based on the solution structure of mouse PrP$^c$ (123–231) and molecular modeling studies, the residues from each of the three α-helical segments which are solvent exposed (accessible to serve as epitopes), as well as those which are solvent inaccessible, were identified. Determination of the solvent-accessible and internal residues permits insertion of the epitope residues into the template in such a way that the same solvent-exposed face of the epitope α-helix is presented in the synthetic polypeptide based on the template.

FIGS. 4A–4B show synthetic polypeptides formed using helix-1 (SEQ ID NO:5) (FIG. 4A) and helix-3 (SEQ ID NO:7) (FIG. 4B) of mouse $PrP^c$. FIG. 4A illustrates insertion of the solvent-accessible residues of mouse $prP^c$ helix-1 into the coiled-coil template. The solvent-inaccessible residues at the a and d positions in the internal region of the α-helix were replaced in favor of Ile and Leu residues, respectively. The construct shown in FIG. 4A for use in formation of a coiled-coil is identified herein as SEQ ID NO:8.

Similarly, as shown in FIG. 4B for helix-3, molecular modeling studies were performed to determined which solven: inaccessible residues in $PrP^c$ could be replaced by appropriate hydrophobic residues for a and d, while ensuring that solvent-exposed residues in the native α-helices are still accessible on the exposed surfaces of the mimetic (positions b, c, e, f and g). The construct in FIG. 4B was made into a covalent two-stranded coiled-coil linked by a disulfide bond formed between the N-termini cysteine residues. Alanine residues were introduced at the N- and C-termini of the construct, as these have a high helical propensity. Arginine residues were added to the C-terminus for increased charge and solubility, and a cysteine residue was introduced at the N-terminus to add stability of two helix-3 coiled-coil domains. This sequence is identified herein as SEQ ID NO:9.

The secondary structure of the designed mimetics prior to disulfide bond formation was evaluated by circular dichroism (CD) spectroscopy. The CD spectrum of an α-helix is characterized by two large negative bands of comparable magnitude near 208 and 222 nm. For a fully helical 14 residue peptide, a molar ellipticity value of approximately $-30{,}700$ deg $cm^2$ $dmol^{-1}$ is expected at 222 nm. FIG. 5 shows the CD spectrum for the non-disulfide bridged H3 construct in FIG. 4B. The spectrum shows that the coiled-coil dimerization motif was highly effective in stabilizing the α-helical structure of all the constructs, as judged by the large negative ellipticity at 222 nm and by comparison to the linear sequence of amino acids not constrained in the template (open circles). The α-helical content of helix-3 coiled-coil construct 12 was calculated to be 81%, based on a value of $-34{,}600$ deg $cM^2$ dmol at 222 nm for a fully α-helical 33 residue peptide. The α-helical content of the disulfide-bridged helix-3 construct approaches 100% since the disulfide bridge eliminates the concentration dependence seen with the non-disulfide bridged form (data not shown). Similarly high α-helical contents were found for the helix-1 and helix-2 coiled-coil stabilized constructs (data not shown).

Since the structure of a number of dimeric coiled-coil domains is known, a molecular model for the helix-3 construct in a coiled-coil scaffold was created by homology modeling. The models showed that the α-helical constraints imposed by the coiled-coil motif on the helix-3 construct results in a structure identical to that of the native helix-3, with positioning of solvent exposed side-chains in the helix-3 construct matching those in native helix-3. These results show that the designed peptides corresponding to the three α-helices of $PrP^c$ have been effectively stabilized in an α-helical conformation with positioning of solvent-exposed side-chains matching those of the native structure and should therefore be appropriate peptidyl mimetics for these elements of secondary structure.

III. Methods of Use

Peptidyl mimetics formed using a selected epitope from an α-helical protein and the template described above find use in a variety of applications, for example as peptides against which antibodies specific to a particular protein conformation can be generated. These applications will row be described.

A. Antibody Generation

In another aspect of the invention, coiled-coil polypeptides prepared as described above are used to generate antibodies against a specific epitope, and more importantly, a specific α-helical conformation of an epitope. This aspect will be described with respect to the prion proteins discussed above, however it will be appreciate that the concept readily extends to other proteins.

Current detection methods for $PrP^C$ and $PrP^{SC}$ rely on polyclonal and monoclonal antibodies which recognize both forms of PrP. Most antibodies in the prior art to date are directed against linear epitopes which are present in both denatured PrP$^C$ and PrP$^{SC}$. In order to distinguish between PrP$^C$ and PrP$^{SC}$ it is therefore necessary to utilize a procedure involving protease treatment followed by immunodetection on Western blots. While PrP$^C$ is degraded by proteolysis, PrP$^{Sc}$ is largely resistant to proteolysis and gives a signature set of undigestable products PrP27–31 which can then be detected by immunodetection. Since these antibodies only recognize denatured forms of PrP, they can only be used to detect PrP under denaturing conditions such as those used for immunohistology or to detect PrP in extracts from various tissues or fluids. In order to carry out assays for native forms of PrP$^C$ and PrP$^{SC}$, it is necessary to develop ligands which will selectively recognize the respective forms of these proteins.

Figure 4A:
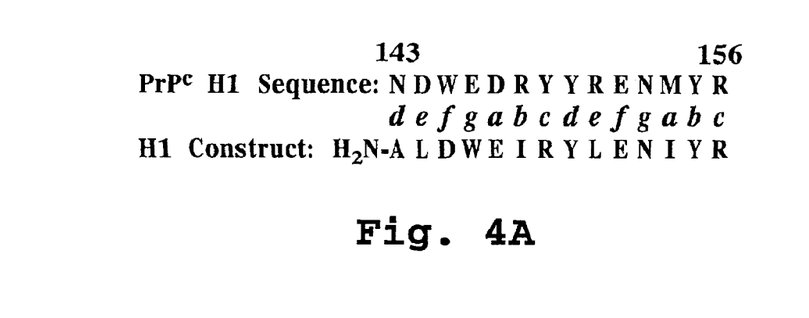
FIGS. 4A–4B shows synthetic peptides formed from mouse prion helix-1 (FIG. 4A) and mouse prion helix-3 (FIG. 4B)
Figure 4B:
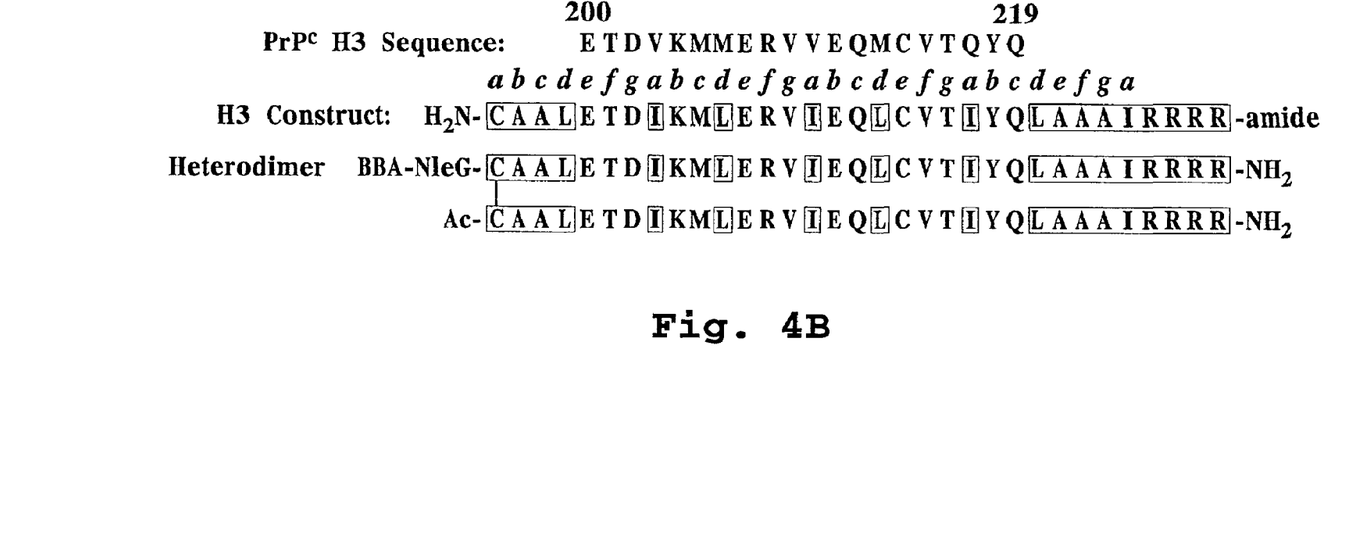
Figure 5:
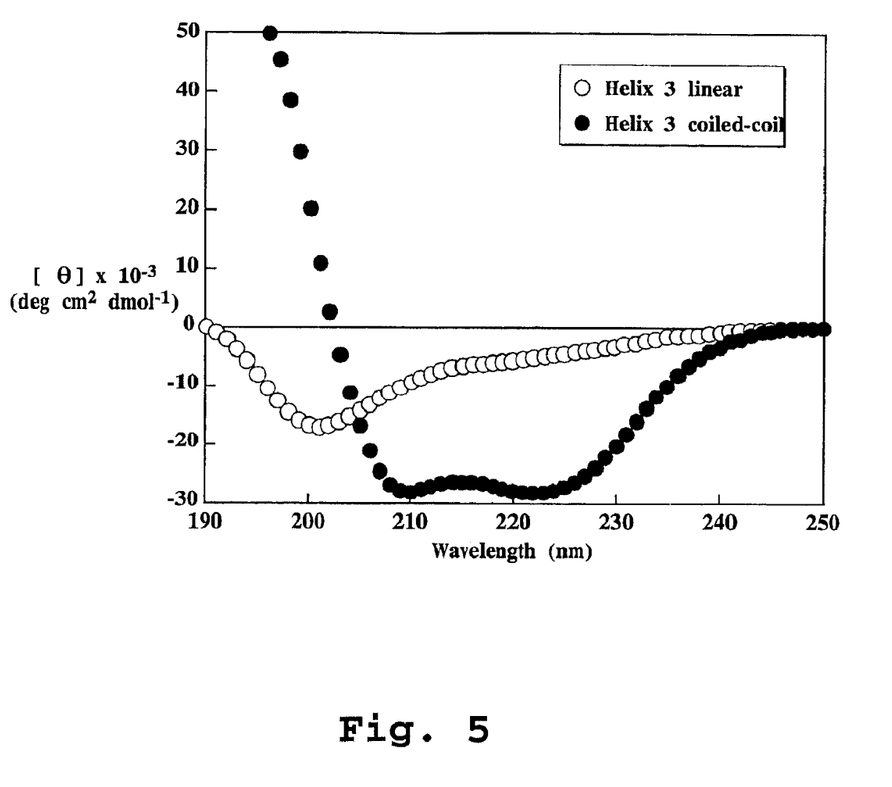
FIG. 5 shows a circular dichroism (CD) spectrum of the synthetic polypeptide coiled-coil construct of FIG. 4B (closed circles) and of a linear, single chain (non-coiled-coil) polypeptide construct (open circles).

In studies performed in support of the present invention, coiled-coil polypeptides were prepared using the three α-helical regions of mouse PrP$^c$ and the template, as described above with respect to FIGS. 4A–4B. The study performed using helix-3 (H3) will be described. The solvent-exposed residues of helix-3 were inserted in the b, c, e, f, and g positions of the template, forming the H3 construct of FIG. 4B. The heterodimer of FIG. 4B was prepared, where the sequence of the two polypeptide chains were identical except that one of the chains contained glycine (G), norleucine (Nle) and benzoylbenzoic acid (BBA). Norleucine was added to determine the peptide/protein carrier ratio after coupling of the peptide to a carrier, as will be described. The BBA group was added as a non-specific, photolabile, cross-linking agent to link the construct to the carrier protein covalently.

The H3 heterodimer construct (FIG. 4B) was conjugated to keyhole limpet hemocyanin (KLH) and to bovine serum albumin, as described in Example 1A. The KLH-polypeptide conjugate in the presence of Freund's adjuvant was injected into rabbits according to the procedure outlined in Example 1B. Each test animal received a first injection of the KLH-polypeptide in Freunds's Complete adjuvant, followed two weeks later with a second injection of the KLH-polypeptide conjugate in Freund's incomplete adjuvant. Two weeks after the second injection, the serum antibody titer was determined using ELISA, as described in Example 1C.

Sera from all of the test animals strongly recognized the coiled-coil polypeptide construct containing the H3 α-helix coupled to BSA at titers of 1:100,000. Thus, all rabbits with the KLH-polypeptide conjugate produced excellent titers of antibodies to the peptide.

As a comparative control, the BBA-Nle-Gly-polypeptide chain was coupled to BSA. The single polypeptide chain does not form an α-helix or a coiled-coil structure and it was found that antibodies did not bind to the single polypeptide chain. This result proves that antibodies can only bind to the H3 sequence when it is in an α-helical conformation, which only occurs when it forms a two-stranded coiled-coil structure.

In light of these results, it will be appreciated that coiled-coil polypeptide constructs formed as described herein, with the solvent-accessible residues inserted into the coiled-coil template, provide a method to constrain the epitope in the necessary configuration for generation of antibodies that specifically recognize the α-helical conformation. The antibodies can be used as diagnostic ligands. For example, in the case of prion proteins, the antibodies selectively bind back to the coiled-coil construct as well as to the native mouse PrP$^c$. Thus, the antibody ligands are useful for detecting the presence of PrP$^c$, and for defining structural changes occurring in PrP$^{sc}$. Ligands which bind to PrP$^c$ and not to PrP$^{sc}$ will indicate which helix has undergone a structural change (perhaps to β-sheet structure). Ligands which bind to both PrP$^c$ as well as PrP$^{sc}$ will indicate that that helix has not undergone a structural change. This information, along with the proposed model of PrP$^{sc}$ (Huang, Z., et in al. *Folding & Design* 1:13–19, 1995) allow determination of which helices should be constrained into a β-sheet conformation for generation of PrP$^{sc}$ mimetics.

From the foregoing, it can be seen how various objects and features of the invention are met. The composition of the ad invention comprised of a selected epitope from an α-helical region of a protein in a particular conformation is inserted into a coiled-coil template for display. It will be appreciated by those of skill in the art that epitopes from a wide range of α-helical proteins can be inserted into the template. The tertiary structure and sequence of thousands of proteins are readily available. Additionally, various software programs enable prediction of α-helical epitopes in proteins. Thus, a wide variety of proteins are suitable, and contemplated for use. In particular, proteins like the prions that have more than one conformation and in their native state are not in a coiled-coil, are preferred. Epitopes from such proteins can be inserted into the template to stabilize and constrain the epitope in an α-helical conformation. The construct is then used to generate antibodies which are specific to the α-helical conformation. These specific antibodies have value in diagnostic and therapeutic applications, as will be appreciated by those of skill in the art.

IV. EXAMPLES

The following examples further illustrate the invention described herein and are in no way intended to limit the scope of the invention.

Example 1

Production of Antibodies to Prion Helix-3 Construct

A. Conjugation of Heterodimer H$_3$Construct to BSA and KLH 12 mg of bovine serum albumin (BSA; Sigma RIA grade) and keyhole limpet hemocyanin (KLH; Sigma) were weighed into separate test tubes (10 mm×75 mm). 8 mg of the coiled-coil heterodimer construct shown in FIG. 4B (SEQ ID NO:9) was added to each tube.

To the tube containing the BSA, 75 µl of 100 mM bicarbonate was added. To the tube containing the KLH, 100 µl of guanidne HCl (6 mM) was added. The tubes were stirred with a capillary tube, smearing the paste onto the sides of the tube. The mixture in each tube was then photolysed for 1 hour in a Rayonet preparative reactor.

The BSA-polypeptide conjugate was dissolved with 6 M urea (5 ml) and then transferred to a dialysis bag and dialysed for 24 hours in 6 M urea, 24 hours in 1 M urea, 24 hours in 100 mM bicarbonate and 24 hours in 10 mM bicarbonate. The KLH-polypeptide conjugate was dissolved in 6 M guanidine HCl (5 mL) and transferred to a dialysis bag and dialysed according to tine procedure of the BSA-polypeptide conjugate.

After dialysis, each conjugate was transferred to a 5 dram vial and the dialysis bags were rinsed with water, to a final volume of 7 mL. A 30 µL sample was removed from each preparation for amino acid analysis and the remainder was freeze dried until use.

B. Administration of KLH-Polypeptide Conjugate to Rabbits

A small sample of each of the five test rabbit's blood was taken for use as pre-immune sera to confirm that none of the rabbits had antibodies against the test antigen prior to immunization. The blood sample was placed in a centrifugation tube and set at room temperature to clot. The sera was separated from the clotted red blood cells by centrifugation at 3600 rpm for 3–5 minutes. The sera was decanted and the clot was discarded. The sera was stored frozen until use by freezing first at −20° C. for 24 hours and then at −70° C. until use.

The KLH-polypeptide conjugate was prepared for injection by mixing 500 μg of the conjugate in 0.5 mL sterile phosphate-buffered saline. The conjugate was drawn into a 3 or 5 mL glass syringe and a micro-emulsifying needle was attached. Another syringe with 0.5 mL of Freund's Complete adjuvant was attached and the conjugate was bolused into the adjuvant. The mixture was pushed back and forth between the connected syringes until the ah mixture was white in color and had the consistency of mayonnaise.

The mixture was injected subcutaneously or intramuscularly into each test rabbit, with the maximum amount administered being 0.25 mL×4 sites s.c. or 0.5 mL !M. Two weeks after this first injection, the rabbits were injected with the KLE-polypeptide 39 mixed with Freund's Incomplete adjuvant, prepared as described above.

Two weeks after the second injection, the rabbits were bled and the antibody titer was determined using ELISA.

C. Detection of Serum Antibodies by ELISA

The ELISA plates were coated w-th BSA-polypeptide conjugates (100 μL per well) at a peptide concentration of 0.2 μg/mL in 100 mM sodium carbonate buffer at pH 9.5. The plates were incubated overnight at 4° C. and then washed five times with phosphate buffered saline (PBS) at pH 7.5 (200 μL/well). The plates were blocked with 5% BSA in TPBS, pH 7.5, for 1 hour at 37° C. (100 μl/well), after which the plates were again washed five times with PBS buffer.

Sera from each of the five test animals was diluted in buffer to concentrations of 1/1,000; 1/10,000; 1/100,000 and 1/1,000,000. The same concentrations of pre-immune sera was used as controls. 100 μL of each dilution was added to a well and the plate was incubated for 2 hours at 37° C. After incubation, unbound antibody was washed out using PBS buffer (3×).

A second antibody, goat anti-rabbit IgG-horse radish peroixdase conjugate (Jackson Labs), was diluted 1:5000 in PBS and 100 μL was added to each well. The plate was incubated for 1 hour at 37° C. After incubation, the antibody was washed from the wells by rinsing 5 times with PBS.

Color development was carried out at room temperature for 30 minutes with agitation. 2,2-azino-di-(3-ethylbenzthiazonine sulfonic acid (ABTS; 24 mg) was dissolved in 40 mL of 100 mM citrate buffer, pH 4.2, containing 30% hydrogen peroxide (40 μL) (150 μL/well). The plates were read at 405 nm at 30 minutes. The background cutoff was calculated by taking the mean value of the control wells and adding 3× the standard deviation of the mean calculated on 30 wells.

Although the invention has been described with respect to particular embodiments, it will be apparent to those skilled in the art that various changes and modifications can be made without departing from the invention.

What it is claimed:

1. A coiled-coil polypeptide comprising the formula $(ab_ic_ide_if_ig_i)_n$, where i=1, 2, ..., n, and n is at least three, said polypeptide being prepared by
   (a) selecting a solvent-accessible region of an epitope of a selected natural protein, wherein said region is not in a coiled-coil conformation in its native state, and inserting the amino acids from said region into the $b_i$, $c_i$, $e_i$, $f_i$ and $g_i$ positions; and
   (b) independently inserting an amino acid selected from the group consisting of leucine, isoleucine, valine, phenylalanine, methionine, tyrosine, and derivatives thereof, into each of the a and d positions such that the amino acids from the epitope in the $b_i$, $c_i$, $e_i$, $f_i$ and $g_i$ positions are interrupted by the amino acids in the a and d positions;

wherein $(ab_ic_ide_if_ig_i)_n$, forms a coiled-coil.

2. The polypeptide of claim 1, wherein a is isoleucine and d is leucine.

3. The polypeptide of claim 1, wherein the coiled-coil polypeptide is comprised of two polypeptide chains arranged in a parallel configuration.

4. The polypeptide of claim 1, wherein n is between about 3 and about 20.

5. The polypeptide of claim 1, wherein the epitopes are selected from α-helical surface regions of a cellular prion protein.

6. The polypeptide of claim 5, wherein the epitopes are selected from exposed surface regions of an infectious prion protein.

7. The polypeptide of claim 5, wherein the sequence formed by the positions $(b_ic_ie_if_ig_i)_n$ corresponds to the solvent-accessible residues of an epitope having a sequence selected from the group consisting of SEQ ID NO: 5, SEQ ID NO: 6, and SEQ ID NO: 7.

8. The polypeptide of claim 5, wherein the cellular prion protein is selected from the group consisting of mouse, hamster, bovine, ovine and human cellular prion proteins.

9. A coiled-coil polypeptide, comprising an amino acid sequence represented by $(ab_ic_ide_if_ig_i)_n$, where i=1, 2, . . . , n, and n is at least three;

a and d are amino acids each independently selected from the group consisting of leucine, isoleucine, valine, phenylalanine, methionine, tyrosine and derivatives thereof;

$(b_ic_ie_if_ig_i)_n$ is a sequence of amino acids from a solvent-accessible region of an epitope from a selected natural protein, wherein said region is not in a coiled-coil conformation in its native state, and the sequence $(b_ic_ie_if_ig_i)_n$ is interrupted by the amino acids in the a and d positions in $(ab_ic_ide_if_ig_i)_n$; and wherein $(ab_ic_ide_if_ig_i)_n$ forms a coiled coil.

10. The polypeptide of claim 9, wherein a is isoleucine and d is leucine.

11. The polypeptide of claim 9, wherein the coiled-coil polypeptide is comprised of two polypeptide chains arranged in a parallel configuration.

12. The polypeptide of claim 9, wherein n is between about 3 and about 20.

13. The polypeptide of claim 9, wherein the epitopes are selected from α-helical surface regions of a cellular prion protein.

14. The polypeptide of claim 9, wherein the epitopes are selected from exposed surface regions of an infectious prion protein.

15. The polypeptide of claim 13, wherein the sequence formed by the positions $(b_ic_ie_if_ig_i)_n$ corresponds to the solvent-accessible residues of an epitope having a sequence selected from the group consisting of SEQ ID NO: 5, SEQ D NO: 6, and SEQ ID NO: 7.

16. The polypeptide of claim 13, wherein the cellular prion protein is selected from the group consisting of mouse, hamster, bovine, ovine and human cellular prion proteins.

17. A coiled-coil polypeptide comprising the formula $(ab_ic_ide_if_ig_i)$, where i=1, 2 . . . , n, and n is between about 5 and about 10, said polypeptide being prepared by (a) selecting a solvent-accessible region of an epitope of a selected natural protein, wherein said region is not in a coiled-coil conformation in its native state, and inserting the amino acids from said region into the $b_i$, $c_i$, $e_i$, $f_i$ and $g_i$ positions; and (b) independently inserting an amino acid selected from the group consisting of leucine, isoleucine, valine, phenylalanine, methionine, tyrosine, and derivatives thereof, into each of the a and d positions such that the amino acids from the epitope in the $b_i$, $c_i$, $e_i$, $f_i$ and $g_i$ positions are interrupted by the amino acids in the a and d positions;

wherein $(a b_i c_i d e_i f_i g_i)_n$ forms a coiled-coil.

18. The polypeptide of claim 17, wherein a is isoleucine and d is leucine.

19. The coiled-coil polypeptide of claim 17, wherein the coiled-coil polypeptide is comprised of two polypeptide chains arranged in a parallel configuration.

20. The polypeptide of claim 17, wherein the epitopes are selected from α-helical surface regions of a cellular prion protein.

21. The

SEQUENCE LISTING

```
<160> NUMBER OF SEQ ID NOS:  9

<210> SEQ ID NO 1
<211> LENGTH: 45
<212> TYPE: PRT
<213> ORGANISM: human

<400> SEQUENCE: 1

Gly Leu Gly Gly Tyr Met Leu Gly Ser Ala Met Ser Arg Pro Ile Ile
 1               5                  10                  15

His Phe Gly Ser Asp Tyr Glu Asp Arg Tyr Tyr Arg Glu Asn Met His
                20                  25                  30

Arg Tyr Pro Asn Gln Val Tyr Tyr Arg Pro Met Asp Glu
            35                  40                  45

<210> SEQ ID NO 2
<211> LENGTH: 45
<212> TYPE: PRT
<213> ORGANISM: mouse

<400> SEQUENCE: 2

Gly Leu Gly Gly Tyr Met Leu Gly Ser Ala Met Ser Arg Pro Met Ile
 1               5                  10                  15

His Phe Gly Asn Asp Trp Glu Asp Arg Tyr Tyr Arg Glu Asn Met Tyr
                20                  25                  30
```

```
Arg Tyr Pro Asn Gln Val Tyr Tyr Arg Pro Val Asp Gln
        35                  40                  45

<210> SEQ ID NO 3
<211> LENGTH: 45
<212> TYPE: PRT
<213> ORGANISM: sheep

<400> SEQUENCE: 3

Gly Leu Gly Gly Tyr Met Leu Gly Ser Ala Met Ser Arg Pro Leu Ile
1               5                   10                  15

His Phe Gly Asn Asp Tyr Glu Asp Arg Tyr Tyr Arg Glu Asn Met Tyr
            20                  25                  30

Arg Tyr Pro Asn Gln Val Tyr Tyr Arg Pro Val Asp Arg
        35                  40                  45

<210> SEQ ID NO 4
<211> LENGTH: 45
<212> TYPE: PRT
<213> ORGANISM: bovine

<400> SEQUENCE: 4

Gly Leu Gly Gly Tyr Met Leu Gly Ser Ala Met Ser Arg Pro Leu Ile
1               5                   10                  15

His Phe Gly Asn Asp Tyr Glu Asp Arg Tyr Tyr Arg Glu Asn Met His
            20                  25                  30

Arg Tyr Pro Asn Gln Val Tyr Tyr Arg Pro Val Asp Gln
        35                  40                  45

<210> SEQ ID NO 5
<211> LENGTH: 14
<212> TYPE: PRT
<213> ORGANISM: mouse

<400> SEQUENCE: 5

Asn Asp Trp Glu Asp Arg Tyr Tyr Arg Glu Asn Met Tyr Arg
1               5                   10

<210> SEQ ID NO 6
<211> LENGTH: 14
<212> TYPE: PRT
<213> ORGANISM: mouse

<400> SEQUENCE: 6

Cys Val Asn Ile Thr Ile Lys Gln Thr Val Thr Thr Thr Thr
1               5                   10

<210> SEQ ID NO 7
<211> LENGTH: 20
<212> TYPE: PRT
<213> ORGANISM: mouse

<400> SEQUENCE: 7

Glu Thr Asp Val Lys Met Met Glu Arg Val Val Glu Gln Met Cys Val
1               5                   10                  15

Thr Gln Tyr Gln
            20

<210> SEQ ID NO 8
<211> LENGTH: 14
<212> TYPE: PRT
<213> ORGANISM: Artificial Sequence
```

-continued

```
<220> FEATURE:
<223> OTHER INFORMATION: construct

<400> SEQUENCE: 8

Ala Leu Asp Trp Glu Ile Arg Tyr Leu Glu Asn Ile Tyr Arg
 1               5                  10

<210> SEQ ID NO 9
<211> LENGTH: 33
<212> TYPE: PRT
<213> ORGANISM: Artificial Sequence
<220> FEATURE:
<223> OTHER INFORMATION: construct

<400> SEQUENCE: 9

Cys Ala Ala Leu Glu Thr Asp Ile Lys Met Leu Glu Arg Val Ile Glu
 1               5                  10                  15

Gln Leu Ser Val Thr Ile Tyr Gln Leu Ala Ala Ala Ile Arg Arg Arg
            20                  25                  30

Arg
```